US009976948B2

(12) United States Patent
Motokawa (10) Patent No.: US 9,976,948 B2
(45) Date of Patent: May 22, 2018

(54) PHASE SEPARATION OBSERVATION METHOD, PHASE SEPARATION OBSERVATION APPARATUS, ANNEALING APPARATUS, AND PRODUCING METHOD FOR SUBSTRATE

(71) Applicant: TOSHIBA MEMORY CORPORATION, Tokyo (JP)

(72) Inventor: Takeharu Motokawa, Kanagawa (JP)

(73) Assignee: Toshiba Memory Corporation, Tokyo (JP)

( * ) Notice: Subject to any disclaimer, the term of this patent is extended or adjusted under 35 U.S.C. 154(b) by 416 days.

(21) Appl. No.: 14/644,681

(22) Filed: Mar. 11, 2015

(65) Prior Publication Data

US 2016/0061716 A1  Mar. 3, 2016

(30) Foreign Application Priority Data

Sep. 2, 2014  (JP) .................. 2014-178411

(51) Int. Cl.

| G01N 21/23 | (2006.01) |
|---|---|
| G01N 21/41 | (2006.01) |
| B29C 35/02 | (2006.01) |
| G01N 21/45 | (2006.01) |

(52) U.S. Cl.
CPC ............. *G01N 21/23* (2013.01); *G01N 21/45* (2013.01)

(58) Field of Classification Search
CPC ......... G01N 21/23; G01N 21/45; B29C 35/02
See application file for complete search history.

(56) References Cited

U.S. PATENT DOCUMENTS

| 3,902,805 A * | 9/1975 | Redner ................... G01N 21/23 250/225 |
|---|---|---|
| 4,749,854 A * | 6/1988 | Martens ................. G01D 5/344 250/225 |
| 4,970,385 A * | 11/1990 | Tatsuno ................... G01K 5/52 250/225 |
| 5,319,194 A * | 6/1994 | Yoshizumi ............. G01N 21/23 250/225 |
| 5,426,505 A * | 6/1995 | Geiser .................... G01N 21/45 356/128 |
| 5,956,146 A * | 9/1999 | Nakagawa ............. G01N 21/23 356/365 |
| 6,268,914 B1 * | 7/2001 | Wang ..................... G01N 21/23 356/243.1 |
| 6,473,179 B1 * | 10/2002 | Wang ........................ G01J 4/04 356/364 |
| 6,985,227 B2 * | 1/2006 | Wang ........................ G01J 4/04 356/364 |

(Continued)

FOREIGN PATENT DOCUMENTS

| JP | 2000-057948 | 2/2000 |
|---|---|---|
| JP | 3940376 | 7/2007 |

*Primary Examiner* — Alison L Hindenlang
*Assistant Examiner* — Emmanuel S Luk
(74) *Attorney, Agent, or Firm* — Finnegan, Henderson, Farabow, Garrett & Dunner, L.L.P.

(57) ABSTRACT

A phase separation observation method according to one embodiment includes determining a progress degree of phase separation of a self-assembly material layer. The progress degree is determined based on the birefringence amount of an observation object. The observation object includes a substrate, and a self-assembly material layer formed on the substrate.

6 Claims, 7 Drawing Sheets

(56) References Cited

U.S. PATENT DOCUMENTS

| | | | |
|---|---|---|---|
| 2004/0095865 A1* | 5/2004 | Katayama | G01N 21/23 369/53.28 |
| 2004/0233434 A1* | 11/2004 | Wang | G01J 4/04 356/365 |
| 2005/0219528 A1* | 10/2005 | Wang | G01N 21/23 356/365 |
| 2006/0291779 A1* | 12/2006 | Schulz | G01N 21/0303 385/37 |
| 2008/0050659 A1 | 2/2008 | Ohtake et al. | |
| 2008/0252898 A1* | 10/2008 | Pfaff | G01B 11/2441 356/457 |
| 2009/0061527 A1* | 3/2009 | Schwartz | C12Q 1/6825 436/94 |
| 2009/0306311 A1 | 12/2009 | Reed | |
| 2013/0123985 A1* | 5/2013 | Hirai | G01N 21/21 700/259 |
| 2013/0215362 A1* | 8/2013 | Koike | G01N 21/23 349/62 |
| 2013/0250277 A1* | 9/2013 | Wang | G01L 1/24 356/33 |
| 2013/0330674 A1 | 12/2013 | Ohtake et al. | |

* cited by examiner

PHASE SEPARATION OBSERVATION METHOD, PHASE SEPARATION OBSERVATION APPARATUS, ANNEALING APPARATUS, AND PRODUCING METHOD FOR SUBSTRATE

CROSS REFERENCE TO RELATED APPLICATION(S)

This application is based upon and claims the benefit of priority from the prior Japanese Patent Application No. 2014-178411, filed on Sep. 2, 2014, the entire contents of which are incorporated herein by reference.

FIELD

Embodiments described herein relate generally to a phase separation observation method, a phase separation observation apparatus, an annealing apparatus, and a producing method for a substrate.

BACKGROUND

In recent years, use of directed self-assembly (DSA) has received attention as a fine patterning technique. In a pattern formation method using DSA, a self-assembly material such as a block copolymer (BCP) is applied onto a guide pattern and microphase-separated to form a microphase separation pattern along the guide pattern.

In the pattern formation method, it is important to observe a progress degree of phase separation of a self-assembly material for setting conditions for a phase separation process.

DETAILED DESCRIPTION

Embodiments will now be explained with reference to the accompanying drawings. The present invention is not limited to the embodiments.

A phase separation observation method according to one embodiment includes determining a progress degree of phase separation of a self-assembly material layer based on the birefringence amount of an observation object. The observation object includes a substrate, and a self-assembly material layer formed on the substrate.

First Embodiment

A phase separation observation method, a phase separation observation apparatus and an annealing apparatus according to the first embodiment will be described with reference to FIGS. 1 to 8. The basic principle of the phase separation observation method according to this embodiment is that phase separation is observed based on a correlation between a birefringence property and a progress degree of phase separation of a self-assembly material. First, the correlation between the birefringence property and the progress degree of phase separation will be described.

Figure 1:
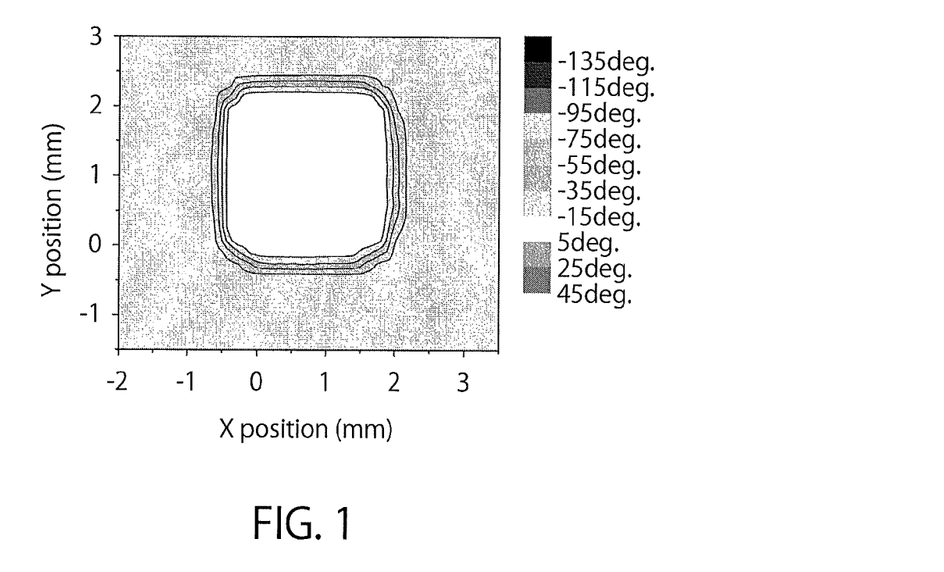
FIG. 1 is a plan view showing a distribution of a main axis azimuth of an observation object.

FIG. 1 is a plan view showing a distribution of a main axis azimuth of an observation object. The observation object in FIG. 1 is a glass substrate on which PS-b-PMMA as a self-assembly material is laminated. PS-b-PMMA is a block copolymer having a birefringence property. The main axis azimuth refers to a gradient of a forward phase axis or retard phase axis with respect to a standard direction.

In FIG. 1, a line-and-space pattern (hereinafter, referred to as a "LS pattern") from microphase-separated PS-b-PMMA is formed on a region of 2 mm×2 mm, which is centered on (X,Y)=(0.6, 1.2), and a finger print pattern (hereinafter, referred to as a "FP pattern") from microphase-separated PS-b-PMMA is formed on the other region. Hereinafter, in the observation object, a region having a LS pattern formed thereon is referred to as a pattern region, and a region having no LS pattern formed thereon is referred to as a non-pattern region. In the case of the observation object in FIG. 1, the region of 2 mm×2 mm is a pattern region, and the other region is a non-pattern region.

As shown in FIG. 1, the main axis azimuth of the pattern region is substantially −15 to 5 degrees, while the main axis azimuth of the non-pattern region is substantially −95 to −75 degrees. As is apparent from FIG. 1, the pattern region provided with a LS pattern and the non-pattern region provided with a FP pattern have different main axis azimuths.

Figure 2:
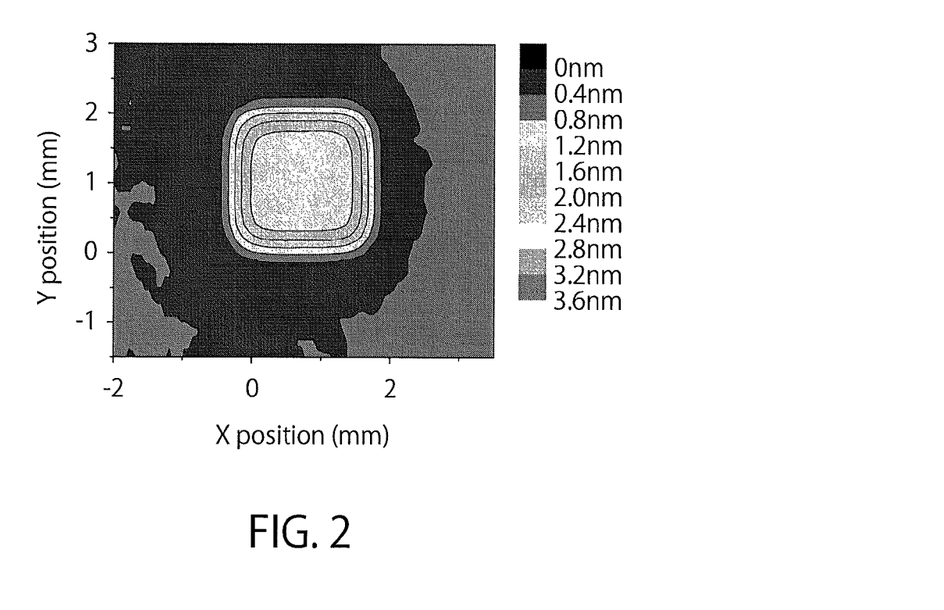
FIG. 2 is a plan view showing a distribution of a retardation of an observation object.

FIG. 2 is a plan view showing a distribution of a retardation (phase difference) of the observation object of FIG. 1. In FIG. 2, the retardation is a product of a birefringence index $\Delta n$ ($=|n_1-n_2|$) and a thickness of an observation object, the birefringence index being an absolute value of a difference between the refractive index $n_1$ of a forward phase axis and the refractive index $n_2$ of a retard phase axis.

As shown in FIG. 2, the retardation of the pattern region is substantially 2.0 to 2.4 nm, while the retardation of the non-pattern region is substantially 0 to 0.8 nm. As is apparent from FIG. 2, the pattern region provided with a LS pattern and the non-pattern region provided with a FP pattern have different retardations.

As shown in FIGS. 1 and 2, the pattern region and the non-pattern region have different main axis azimuths and retardations. This is because in the pattern region, PS-b-PMMA having a birefringence property is regularly arranged, and therefore the birefringence property of PS-b-PMMA is observed over the entire region, while in the non-pattern region, PS-b-PMMA is irregularly arranged, and therefore the birefringence properties of individual PS-b-PMMAs offset one another, so that the birefringence property of PS-b-PMMA is not observed over the entire region. The reason why the retardation is not necessarily 0 nm in the non-pattern region is that the retardation of the observation object includes the birefringence property of the glass substrate.

Thus, the birefringence property of the observation object varies depending on whether or not the self-assembly material having a birefringence property is arranged in the shape of a LS pattern. Specifically, the birefringence property of the observation object is enhanced as formation of the LS pattern progresses. Therefore, when the LS pattern is formed from a self-assembly material having a birefringence property, a progress degree of formation of the LS pattern, i.e. a progress degree of phase separation of the self-assembly material can be observed by observing the birefringence property of the observation object.

Figure 3:
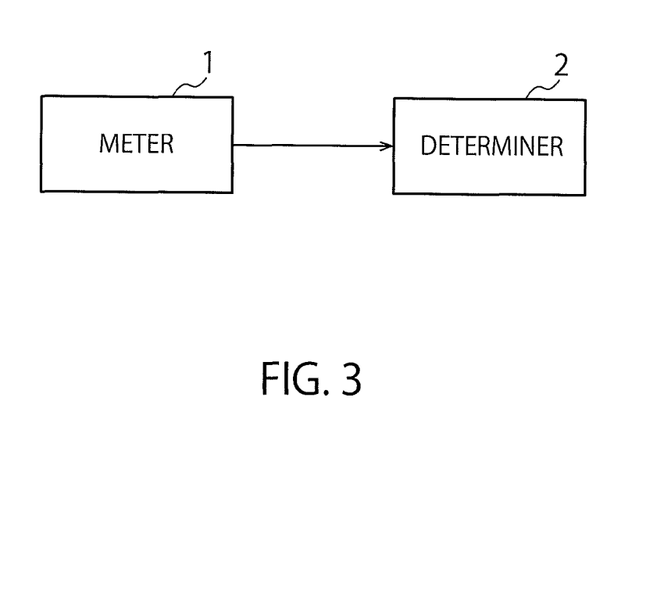
FIG. 3 is a view showing an outline configuration of a phase separation observation apparatus.

A phase separation observation method and a phase separation observation apparatus will now be described in which a progress degree of phase separation is observed based on the above-mentioned basic principle. Here, FIG. 3 is a view showing a function configuration of a phase separation observation apparatus according to this embodiment. As shown in FIG. 3, the phase separation observation apparatus includes a meter 1 and a determiner 2.

The meter 1 measures one or more birefringence amounts in the pattern region of the observation object. The observation object is a substrate having a self-assembly material layer containing a self-assembly material. The self-assembly material is, for example, a block copolymer such as a diblock copolymer or a triblock copolymer, but is not limited thereto. In any case, the self-assembly material has a birefringence property. The substrate is, for example, a semiconductor substrate, a glass substrate or a quartz glass substrate, but is not limited thereto.

The birefringence amount is a value showing a magnitude of the birefringence property. The birefringence amount is, for example, a main axis azimuth, a retardation or a birefringence index, but is not limited thereto. The retardation may be a product of a birefringence and a thickness of a substrate (nm), or may be a phase difference (deg).

As the meter 1, any birefringence measurement device appropriate to an observation object can be used. As a method for measuring a birefringence by the meter 1, any measurement method such as a rotary analyzer method, a phase compensation method, a Senarmont method, a phase modulation method or an optical heterodyne interferometry can be used.

The determiner 2 determines a progress degree of phase separation of a self-assembly material based on the birefringence amount measured by the meter 1. More specifically, the determiner 2 acquires a birefringence amount from the meter 1, and compares the acquired birefringence amount with a previously stored progress degree model to determine a progress degree of phase separation.

Figure 4:
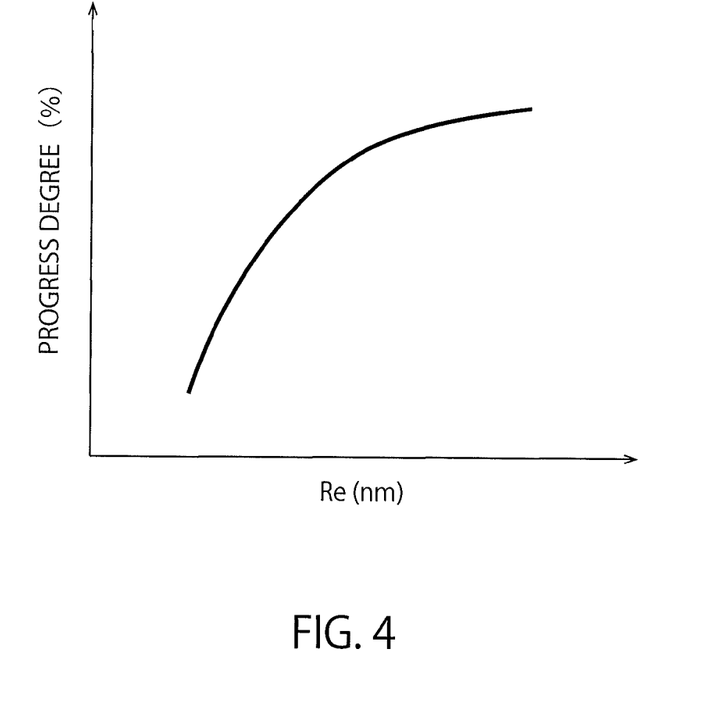
FIG. 4 is a graph showing one example of a progress degree model.

The progress degree model is a model showing a relationship between a birefringence amount and a progress degree of phase separation. The progress degree model is prepared based on experiments in advance, and then stored in the determiner 2. FIG. 4 is a graph showing one example of the progress degree model. In FIG. 4, the abscissa represents a retardation, and the ordinate represents a progress degree of phase separation. The progress degree model may be prepared for each birefringence amount to store a plurality of progress degree models in the determiner 2.

Figure 5:
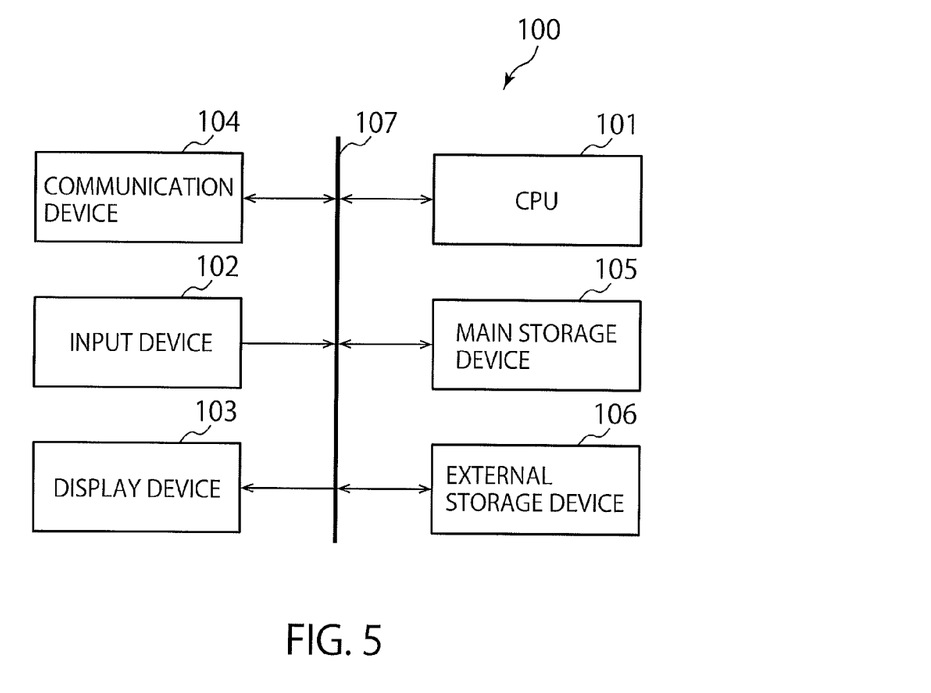
FIG. 5 is a view showing an outline configuration of a computer device that forms a determiner.

The determiner 2 includes a computer device 100. Here, FIG. 5 is a block diagram showing the computer device 100. As shown in FIG. 5, the computer device 100 includes a CPU 101, an input device 102, a display device 103, a communication device 104, a main storage device 105 and an external storage device 106, and these devices are mutually connected via a bus 107.

The CPU (central processing unit) 101 executes a progress degree determination program on the main storage device 105. The progress degree determination program is a program that realizes the function of the determiner 2. When the CPU 101 executes the progress degree determination program, the function of the determiner 2 is realized.

The input device 102 is a device for inputting data and instructions to the determiner 2 from the outside. The input device 102 may be a device for the user to perform inputting directly, such as a keyboard, a mouse or a touch panel. The input device 102 may be a device that enables inputting from an external device, such as a USB, or software.

The display device 103 is a display that displays an image signal outputted from the determiner 2. The display device is, for example, a LCD (liquid crystal display), a CRT (brown tube) or a PDP (plasma display), but is not limited thereto. Results of determination by the determiner 2 can be displayed via the display device 103.

The communication device 104 is a device for the determiner 2 to communicate with an external device such as the meter 1 by a predetermined communication method. The determiner 2 performs wireless communication or wire communication with an external device through the communication device 104. The communication device 104 is, for example, a modem or a router, but is not limited thereto. Information such as a birefringence amount can be inputted from the meter 1 through the communication device 104.

In execution of the progress degree determination program, the main storage device 105 stores the progress degree determination program, data required for execution of the progress degree determination program, data generated by execution of the progress degree determination program, and so on. The progress degree determination program is developed and executed on the main storage device 105. The main storage device 105 is, for example, RAM, DRAM or SRAM, but is not limited thereto. The progress degree model is stored in at least one of the main storage device 105 and the external storage device 106. The main storage device 105 may store OS, BIOS and various kinds of middleware for the computer device.

The external storage device 106 stores the progress degree determination program, data required for execution of the progress degree determination program, data generated by execution of the progress degree determination program, and so on. These programs and data are read by the main storage device 105 in execution of the progress degree determination program. The external storage device 106 is, for example, a hard disk, an optical disk, a flash memory and a magnetic tape, but is not limited thereto.

The progress degree determination program may be previously installed in the computer device, or may be stored in a storage medium such as CD-ROM. Alternatively, the progress degree determination program may be uploaded on the Internet.

According to the phase separation observation apparatus and phase separation observation method described above, a progress degree of phase separation of a self-assembly material can be directly observed by measuring a birefringence amount of an observation object. In other words, it is not necessary to take out the observation object from the phase separation observation apparatus for determining whether phase separation occurs or not. Accordingly, whether phase separation occurs or not can be quickly determined.

The phase separation observation apparatus may observe progress degrees of phase separation at a plurality of parts of the pattern region of the observation object. Observation accuracy can be hereby improved. The phase separation observation apparatus may observe a progress degree of phase separation of an observation object after completion of the phase separation process, or may observe a progress degree of phase separation of an observation object in the course of the phase separation process.

Further, the phase separation observation apparatus may observe a progress degree of phase separation of an observation object on which a LS pattern of a self-assembly material layer is developed. The development of a LS pattern herein means that a LS pattern is formed on a self-assembly material layer through the phase separation process, and the self-assembly material layer at a space part of the LS pattern is removed.

Figure 6:
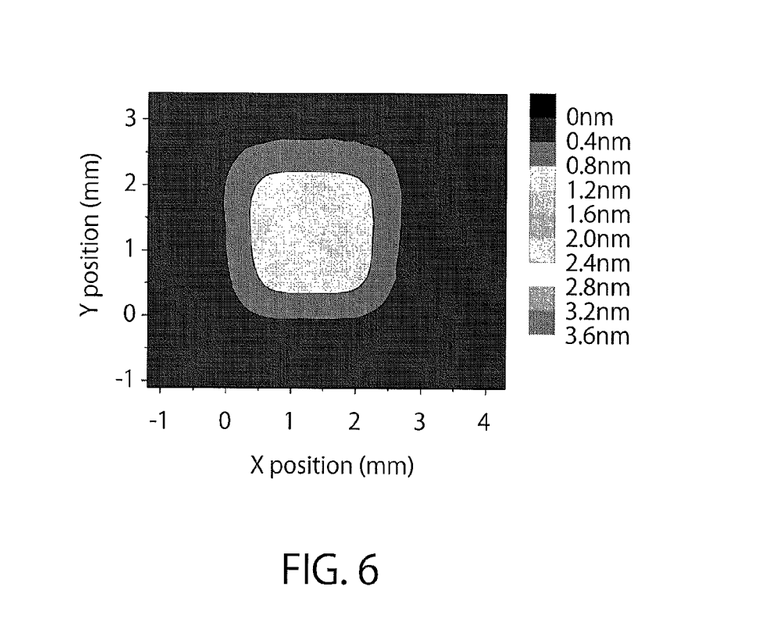
FIG. 6 is a plan view showing a distribution of a retardation of an observation object after development processing.

FIG. 6 is a plan view showing a distribution of a retardation measured after the observation object of FIG. 1 is subjected to development processing. As shown in FIG. 6, the pattern-formed region and the pattern-non-formed region have different retardations. This is because PS (polystyrene) left as a line part has a birefringence property. Thus, even after the observation object is subjected to development processing, a progress degree of phase separation can be observed when the line part of the self-assembly material layer has a birefringence property.

Figure 7:
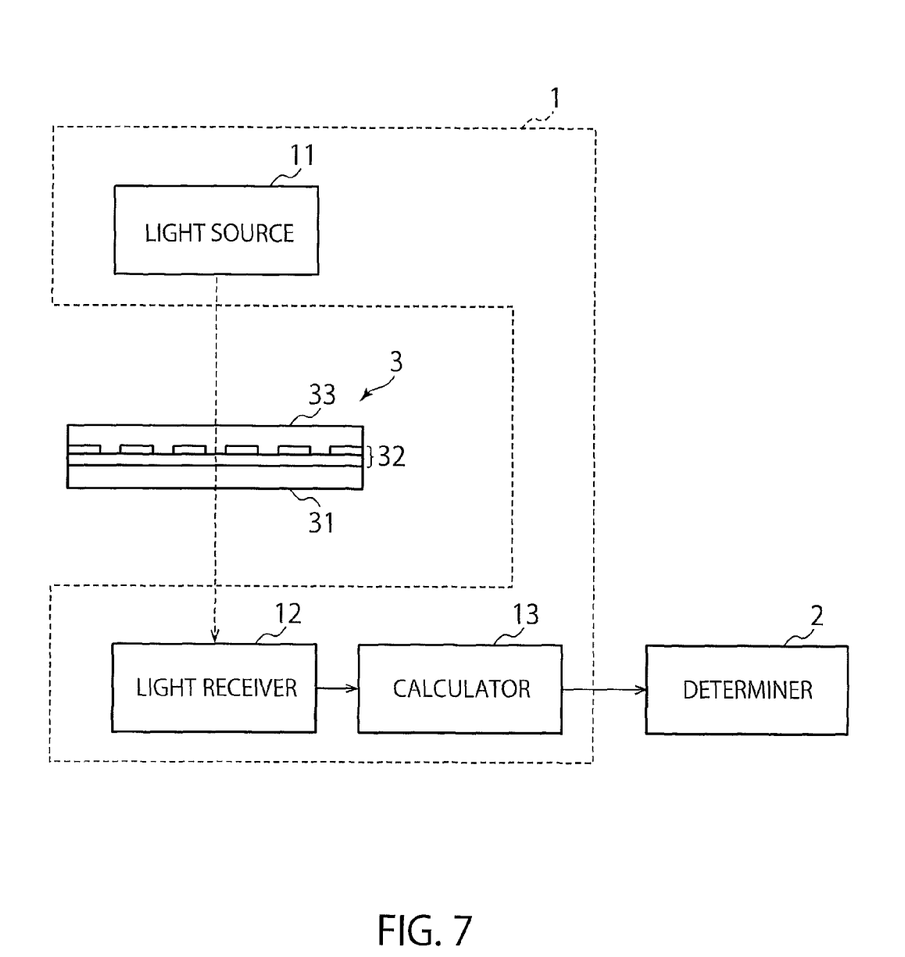
FIG. 7 is a view showing one example of a phase separation observation apparatus.

FIG. 7 is a view showing a specific example of the phase separation observation apparatus according to this embodiment. The meter 1 of the phase separation observation apparatus in FIG. 7 is a birefringence measurement device that measures a birefringence amount by an optical heterodyne interferometry. The meter 1 includes a light source 11, a light receiver 12 and a calculator 13 as shown in FIG. 7, and measures a birefringence amount of an observation object 3.

The light source 11 emits light to the observation object 3, the light being any light that enables a birefringence amount to be measured by an optical heterodyne interferometry. The light emitted by the light source 11 is, for example, two-frequency orthogonal linearly polarized light, but is not limited thereto. The two-frequency orthogonal linearly polarized light is linearly polarized light in which two rays of light having different frequencies cross orthogonal to each other.

The light source 11 is preferably a laser oscillator. This is because energy of laser light is lower than energy of electron beams used in conventional phase separation observation apparatuses, so that degeneration of the observation object 3 is hard to occur in measurement of a birefringence amount. The light source 11 is, for example, a He—Ne laser oscillator with a wavelength of 633 nm, but is not limited thereto.

The light receiver 12 receives light emitted by the light source 11 and passing through the observation object 3. The light receiver 12 outputs an electric signal appropriate to received light. The light receiver 12 is, for example, a photodiode, but is not limited thereto.

The calculator 13 receives an electric signal from the light receiver 12, and calculates a birefringence amount based on the received electric signal. The birefringence amount calculated by the calculator 13 is sent to the determiner 2 as a value of birefringence amount measured by the meter 1. The calculator 13 is, for example, a phase difference meter that calculates a phase difference between two rays of linearly polarized light, but the calculator 13 is not limited thereto.

The observation object 3, of which progress degree of phase separation is observed by the phase separation observation apparatus in FIG. 7, will be described. As shown in FIG. 7, the observation object 3 includes a substrate 31, a guide pattern 32 and a self-assembly material layer 33.

The substrate 31 is a substrate permeable to light emitted by the light source 11. The substrate 31 is, for example, a glass substrate or a quartz glass substrate, but is not limited thereto.

The guide pattern 32 is formed on the substrate 31, and has a LS pattern shape. The guide pattern 32 includes at least one of a chemical guide and a physical guide, and guides a self-assembly material so that the self-assembly material layer 33 is phase-separated in the shape of a LS pattern. In the observation object 3, a region provided with the guide pattern 32 is a pattern region. The guide pattern 32 is formed so as to be permeable to light emitted by the light source 11.

The self-assembly material layer 33 is formed on the guide pattern 32. The self-assembly material layer 33 is permeable to light emitted by the light source 11, and is formed of a self-assembly material having a birefringence property. The self-assembly material is, for example, a block copolymer, but is not limited thereto. The self-assembly material layer 33 has a LS pattern formed along the LS pattern of the guide pattern 32 through the phase separation process (annealing treatment).

The above-mentioned observation object 3 is disposed on an optical path extending from the light source 11 to the light receiver 12. The reason why each part of the observation object 3 is permeable to light emitted by the light source 11 is that in an optical heterodyne interferometry, a birefringence amount is measured using light passing through the observation object 3.

As described above, the meter 1 using an optical heterodyne interferometry can measure a birefringence amount using laser light. Therefore, degeneration of the observation object 3 in measurement of a birefringence amount can be suppressed. The birefringence amount can be hereby measured with high accuracy to improve observation accuracy of a progress degree of phase separation. Since degeneration of the observation object 3 is suppressed, influences on later steps can be suppressed.

The phase separation observation apparatus in FIG. 7 and the phase separation observation method using the apparatus are suitable for observation of phase separation in the production process of a transparent substrate such as a glass substrate or a quartz glass substrate like a photomask or a template for nanoimprint.

Figure 8:
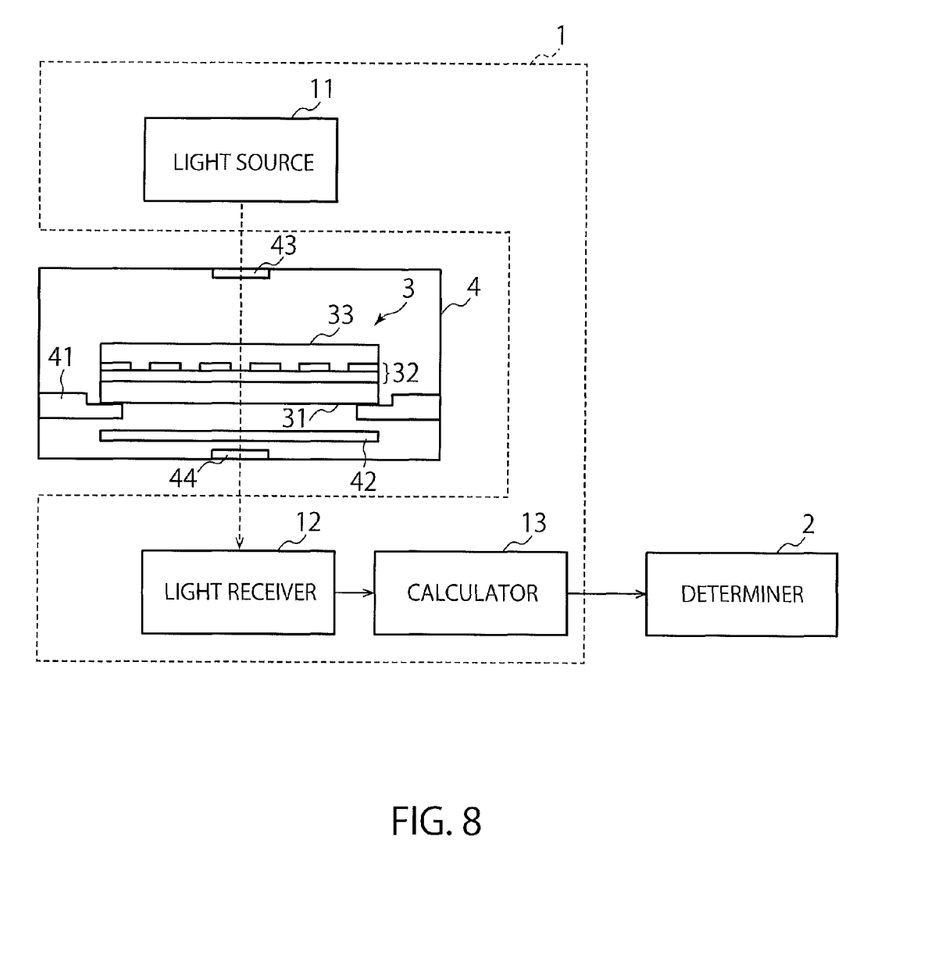
FIG. 8 is a view showing one example of an annealing apparatus.

An annealing apparatus according to this embodiment will now be described. The annealing apparatus according to this embodiment includes the phase separation observation apparatus according to this embodiment, and a chamber 4 for annealing treatment. FIG. 8 is a view showing one example of an annealing apparatus. In FIG. 8, the annealing apparatus includes the phase separation observation apparatus shown in FIG. 7.

The chamber 4, which is a process chamber where the annealing treatment (phase separation process) of the observation object 3 is performed, is disposed between the light source 11 and the light receiver 12. As shown in FIG. 8, the chamber 4 includes a support portion 41, a heater 42, an inlet portion 43 and an outlet portion 44.

The support portion 41 supports the observation object 3 stored in the chamber 4. The support portion 41 is preferably movable. The observation object 3 supported by the support portion 41 can be hereby moved to observe progress degrees of phase separation of a plurality of parts of the observation object 3.

The heater 42 heats the observation object 3 supported by the support portion 41. In FIG. 8, one heater 42 is provided below the observation object, but a plurality of heaters 42 may be provided, or the heater 42 may be provided above or beside the observation object 3. The heater 42 is, for example, a hot plate, but is not limited thereto.

The inlet portion 43 is provided in the chamber 4 on the light source 11 side, and forms an optical path extending from the light source 11 to the light receiver 12. Light emitted from the light source 11 enters the inside of the chamber 4 through the inlet portion 43, and is emitted to the observation object 3. The inlet portion 43 may be a window formed of a transparent material such as glass, or may be a valve or shutter that is opened and closed in synchronization with emission of light from the light source 11.

The outlet portion 44 is provided in the chamber 4 on the light receiver 12 side, and forms an optical path extending from the light source 11 to the light receiver 12. Light passing through the observation object 3 exits the inside of the chamber 4 through the outlet portion 44, and enters the light receiver 12. The outlet portion 44 may be a window formed of a transparent material such as glass, or may be a valve or shutter that is opened and closed in synchronization with emission of light from the light source 11.

The annealing apparatus observes a progress degree of phase separation of the observation object 3 during the annealing treatment (phase separation process) of the observation object 3. The temperature of the inside of the chamber 4, the gas component, and the duration of the annealing treatment are controlled based on the progress degree of phase separation which is determined by the determiner 2. The control can be performed by the computer device 100 that forms the determiner 2.

The annealing apparatus may be configured such that the phase separation observation apparatus and the chamber 4 are integrated with each other, or may be configured such that the phase separation observation apparatus and the chamber 4 for the phase separation observation apparatus are independent of each other. The optical system including the light source 11 and the light receiver 12 of the phase separation observation apparatus may be movable. Progress degrees of phase separation at a plurality of parts of the observation object 3 can hereby observed.

Second Embodiment

A phase separation observation method, a phase separation observation apparatus and an annealing apparatus according to the second embodiment will be described with reference to FIGS. 9 to 11. In this embodiment, the configurations of the phase separation observation apparatus and the annealing apparatus are similar to those in the first embodiment.

In the phase separation observation method according to the first embodiment, a progress degree of phase separation is determined based on the birefringence amount of an observation object, but as described above, the birefringence amount of the observation object includes the birefringence amount of a substrate. Thus, in this embodiment, the birefringence amount of the substrate is subtracted from the birefringence amount of the observation object to calculate a birefringence amount of a self-assembly material layer, and a progress degree of phase separation is determined based on the birefringence amount of the self-assembly material layer.

The birefringence amount of the substrate can be acquired by, for example, performing measurement before the start of the phase separation process. By subtracting the measured value from the birefringence amount of the observation object, the birefringence amount of the self-assembly material layer can be calculated.

The birefringence amount of the substrate can also be estimated from a measured value obtained by measuring a birefringence amount of a non-pattern region of the observation object. Here, FIG. 9 is a plan view showing a distribution of a retardation of the non-pattern region of the observation object of FIG. 1. As described above, a birefringence property of PS-b-PMMA is not observed in the non-pattern region on which a FP pattern is formed. Therefore, the retardation of the non-pattern region shown in FIG. 9 is a retardation of a glass substrate. As shown in FIG. 9, the retardation of the glass substrate is substantially 0 to 0.8 nm.

Figure 9:
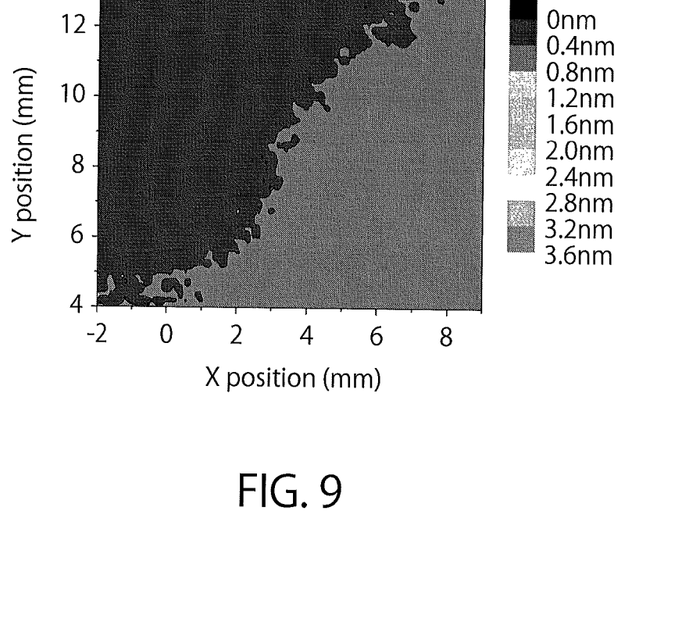
FIG. 9 is a plan view showing a distribution of a retardation of an observation object in a non-pattern region.
Figure 10:
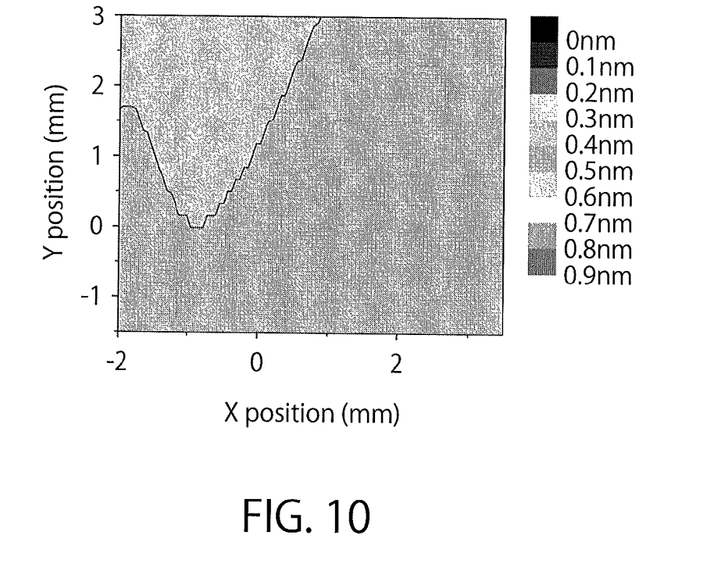
FIG. 10 is a plan view showing an estimated distribution of a retardation of a glass substrate.

FIG. 10 is a plan view showing a distribution of a retardation of a pattern region, which is estimated based on the retardation in FIG. 9. The estimated distribution of the retardation of the pattern region can be estimated by, for example, fitting the distribution of the retardation of the non-pattern region using a least squares method.

Figure 11:
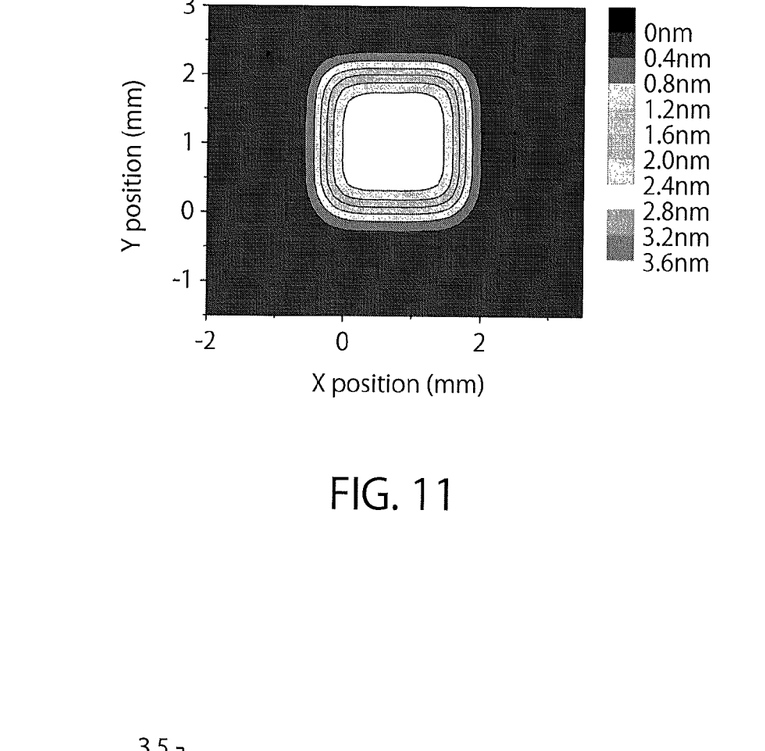
FIG. 11 is a plan view showing an estimated distribution of a retardation of PS-b-PMMA.

FIG. 11 is a plan view showing a distribution of a retardation which is obtained by subtracting the retardation in FIG. 10 from the retardation in FIG. 2. In other words, FIG. 11 shows an estimated distribution of a retardation of PS-b-PMMA of the observation object of FIG. 1. In FIG. 11, the retardation of the non-pattern region is substantially 0 to 0.4 nm, and it is thus apparent that the distribution of the retardation of PS-b-PMMA is accurately estimated.

As described above, by the phase separation observation method according to this embodiment, a progress degree of phase separation can be determined based on the birefringence amount of the self-assembly material layer. Therefore, a progress degree of phase separation can be more accurately determined. Estimation of the birefringence amount of the substrate in the pattern region and calculation of the birefringence amount of the self-assembly material layer can be performed by the computer device 100 that forms the determiner 2.

Third Embodiment

A phase separation observation method according to the third embodiment will be described with reference to FIG. 12. In this embodiment, the configurations of the phase separation observation apparatus and the annealing apparatus are similar to those in the first embodiment. The phase separation observation method according to this embodiment includes determining a size (pitch) of a guide pattern based on a birefringence amount of an observation object.

Figure 12:
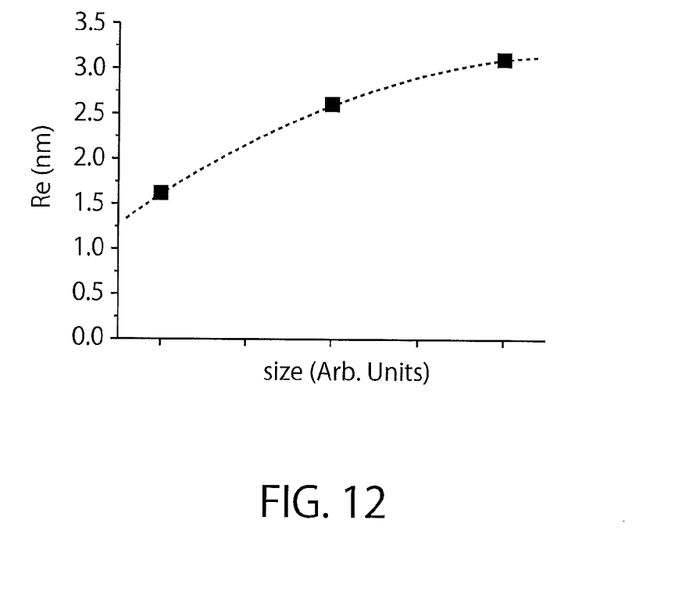
FIG. 12 is a graph showing a relationship between a size of a guide pattern and a retardation of an observation object.

FIG. 12 is a graph showing a relationship between a size of a guide pattern and a retardation of an observation object. In FIG. 12, the abscissa represents a size of the guide pattern, and the ordinate represents a measured value of retardation. In FIG. 12, three measurement results are plotted, and they are measurement results for observation objects having self-assembly material layers containing the same self-assembly material.

As shown in FIG. 12, the retardation of the observation object increases as the size of the guide pattern increases. When the size of the guide pattern is the optimum size of the guide pattern which is predicted based on the pitch of the intrinsic phase separation pattern of the self-assembly material, the retardation becomes maximum.

Thus, when the self-assembly material remains the same, there is a correlation between the size of the guide pattern and the birefringence amount of the observation object. Therefore, when the pitch of the phase separation pattern of the self-assembly material is known, the size of the guide pattern formed on a substrate can be determined by measuring the birefringence amount of the observation object.

Further, the progress degree model can be corrected based on a relationship between the size of the guide pattern and the birefringence amount of the observation object. Consequently, progress degree models of observation objects having guide patterns of various sizes can be prepared based on a progress degree model of an observation object having a guide pattern of a predetermined size.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

The invention claimed is:

1. A phase separation observation method comprising:
   determining a progress degree of phase separation of a self-assembly material layer based on a birefringence amount of an observation object including a substrate, and the self-assembly material layer formed on the substrate; and
   calculating the birefringence amount of the self-assembly material layer based on a birefringence amount of the observation object and a birefringence amount of the substrate, wherein
   the determination of the progress degree of phase separation of the self-assembly material layer is performed based on the birefringence amount of the self-assembly material layer.

2. The method according to claim 1, wherein the self-assembly material layer contains a block copolymer having a birefringence property.

3. The method according to claim 2, wherein the measurement of the birefringence amount is performed using an optical heterodyne interferometry.

4. The method according to claim 1, wherein the determination of the progress degree of phase separation of the self-assembly material layer is performed during or after a phase separation process of the observation object.

5. The method according to claim 1, further comprising determining a size of a guide pattern formed on the substrate, based on a pitch of a phase separation pattern of a self-assembly material that forms the self-assembly material layer, and the birefringence amount of the observation object.

6. The method according to claim 1, wherein the birefringence amount is a main axis azimuth, a retardation, or a birefringence index.

* * * * *